US005824316A

United States Patent [19]
Grubman et al.

[11] Patent Number: 5,824,316
[45] Date of Patent: Oct. 20, 1998

[54] LEADER-PROTEINASE DELETED FOOT-AND-MOUTH DISEASE VIRUSES AND THEIR USE AS VACCINES

[75] Inventors: Marvin J. Grubman, Southold, N.Y.; Peter W. Mason, Killingworth, Conn.; Maria Elisa Piccone, Buenos, Aires, Argentina; Elizabeth Rieder, Westbrook, Conn.

[73] Assignee: The United States of America as represented by the Secretary of Agriculture, Washington, D.C.

[21] Appl. No.: 653,037

[22] Filed: May 24, 1996

[51] Int. Cl.[6] ............................. A61K 39/135; C12N 7/04

[52] U.S. Cl. ........................................ 424/216.1; 435/236

[58] Field of Search ........................... 435/236; 424/216.1

[56] References Cited

PUBLICATIONS

Kirchweger et al., *J. Virology*, 68(9), pp. 5677–5687 (1994).
Piccone et al., Ivth International Positive Strand RNA Virus Symposiu, May 25–30, 1995, Official Abstract Form.
Piccone et al., *J. Virology*, 69(9), pp. 5376–5382 (1995).

*Primary Examiner*—Ponnathapura Achutamurthy
*Assistant Examiner*—Phuong T. Bui
*Attorney, Agent, or Firm*—M. Howard Silverstein; John Fado; Janelle S. Graeter

[57] ABSTRACT

A foot-and-mouth disease virus has been genetically engineered by deleting the nucleic acid sequence encoding the leader (L) proteinase from an infectious cDNA copy of the viral genome and producing an L proteinase-deleted virus. The L proteinase-deleted viruses are able to assemble and grow in cells in culture, but, since they lack L proteinase, they are less toxic to infected cells within the animal, producing an attenuated infection. The recombinant virus can be formulated into an effective vaccine for the prevention of foot-and-mouth disease.

5 Claims, 7 Drawing Sheets

LEADER-PROTEINASE DELETED FOOT-AND-MOUTH DISEASE VIRUSES AND THEIR USE AS VACCINES

BACKGROUND OF THE INVENTION

1. Field of the Invention

Foot-and-mouth disease virus (FMDV) is responsible for one of the most devastating and contagious diseases in cattle and other cloven-hooved animals, affecting over 100,000 animals a year and resulting in significant economic loss. The disease occurs in many areas of the world outside the United States where vaccination programs have been largely effective. There are risks associated with the vaccines currently in use, however, and at present FMDV vaccines cannot be produced in the United States despite the continued threat of the introduction of this agent into the country. It is feared that the virus used to make vaccines could escape from containment and cause disease. Moreover, the failure to completely inactivate the virus during vaccine preparation has led to accidental outbreaks of infection. In addition, there is considerable antigenic variability among the various serotypes, thus some viruses may not be recognized by the vaccinated animals. Furthermore, frequent revaccination has been required in order to maintain protective immunity utilizing conventional vaccines containing virus inactivated by chemical treatment (Bachrach, H. L. 1968. *Annu. Rev. Microbiol.* vol. 22, pp. 201–244). There is thus a strong incentive to develop an effective vaccine which eliminates the threat of infection due to the accidental outbreaks associated with vaccine production and administration. This invention relates to a new vaccine against FMDV which provides effective protection, does not present the risk of causing accidental infections and induces an immune response in vaccinated animals similar to natural infection.

DESCRIPTION OF THE PRIOR ART

In an effort to overcome the deficiencies of conventional virus vaccines, synthetic vaccines have been investigated. Identification of a flexible loop exposed on the virus surface as the main antigenic site of FMDV (site A) prompted investigation into the use of various peptide fragments within site A to stimulate immunological responses. For example, the conserved tripeptide Arg-Gly-Asp (RGD) was evaluated for its ability to stimulate the production of neutralizing antibodies in rabbits or guinea pigs (Novella et al. 1993. *FEBS Letters.* vol. 330, no. 3, pp. 253–259).

Attempts to develop live-attenuated FMD vaccines by classical methods have met with limited success (Bachrach, supra), and the well-known instability of the viral genome (Domingo et al. 1993. *J. Gen. Virol.* vol. 74, pp. 2039–2045) strongly suggests that viruses attenuated by mutation at a limited number of sites could easily revert to virulence. Rieder et al. (1993. *J. Virol.* vol. 67, no. 9, pp. 5139–5145), for example, evaluated the role of the poly(C) tract found at the 5' end of the FMDV genome and reported attempts to attenuate FMDV by deletion of the poly(C) tract near the 5' end of the genome (Rieder et al., supra). Cardioviruses having shorter-than-natural poly(C) tracts had been shown to be dramatically attenuated; however, the poly(C) tract length of FMDV showed no effect on virulence when tested in mice. Viruses having poly(C) tracts of only 2 nucleotides maintained their shortened poly(C) tracts in cell culture and in vivo, and they were virulent in mice (Rieder et al., supra).

Copending patent application (Ser. No. 08/418,716) discloses a novel FMDV which is immunogenic but not infectious. The virus can be prepared by deletion of the nucleic acid sequence encoding the cell binding site from an infectious cDNA copy of the genome.

The search has thus continued for an improved vaccine which is both safe and effective.

SUMMARY OF THE INVENTION

We have discovered that a novel recombinant foot-and-mouth disease virus can be prepared by deleting the nucleic acid sequence encoding the leader (L) proteinase from an infectious cDNA copy of the viral genome to produce a leader-deleted virus. This virus is able to assemble and grow in culture, but, since it lacks the L coding region, it is less toxic to the host and grows more slowly than parental virus. In accordance with this discovery, it is an object of the invention to provide a novel genetically-engineered foot-and-mouth disease virus which is capable of providing protective immunity against foot-and-mouth disease.

It is an additional object of the invention to provide a novel recombinant FMDV genomic RNA which encodes a leaderless FMD virus.

It is a further object of the invention to provide a novel recombinant FMDV cDNA which lacks the sequence encoding the leader (L) proteinase.

It is also an object of the invention to provide a novel FMD vaccine capable of providing protective immunity against foot-and-mouth disease.

It is another object of the invention to provide a method of conferring immunological protection against foot-and-mouth disease by administering the novel vaccine.

Other objects and advantages of the invention will become readily apparent from the following description.

Cell extracts were prepared, immunoprecipitated with bovine convalescent serum (lanes 1–6) or MAb 2PD11 (lanes 8–13), and analyzed by SDS-PAGE on a 15% gel. Lane 7 contains in vitro translation products of FMD virion RNA.

Figure 4:
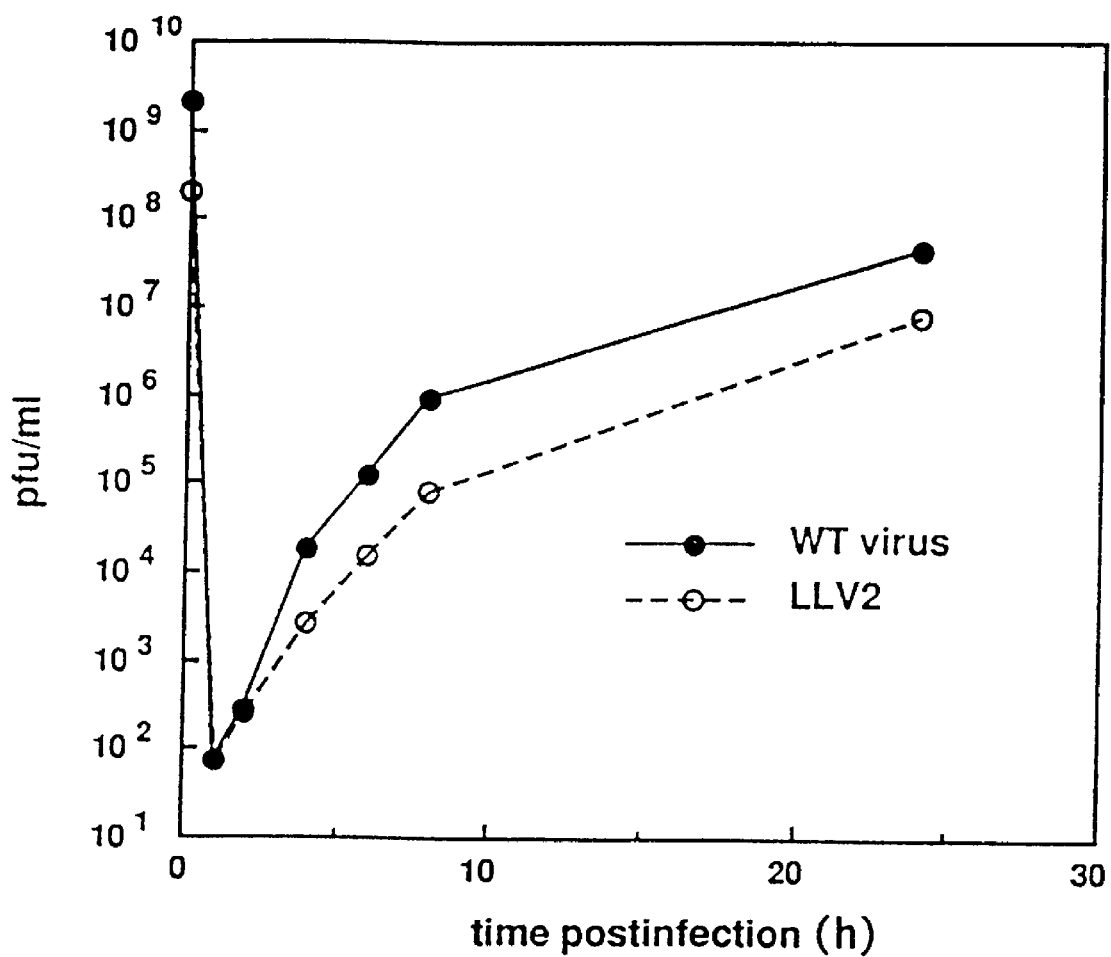
Figure 5:
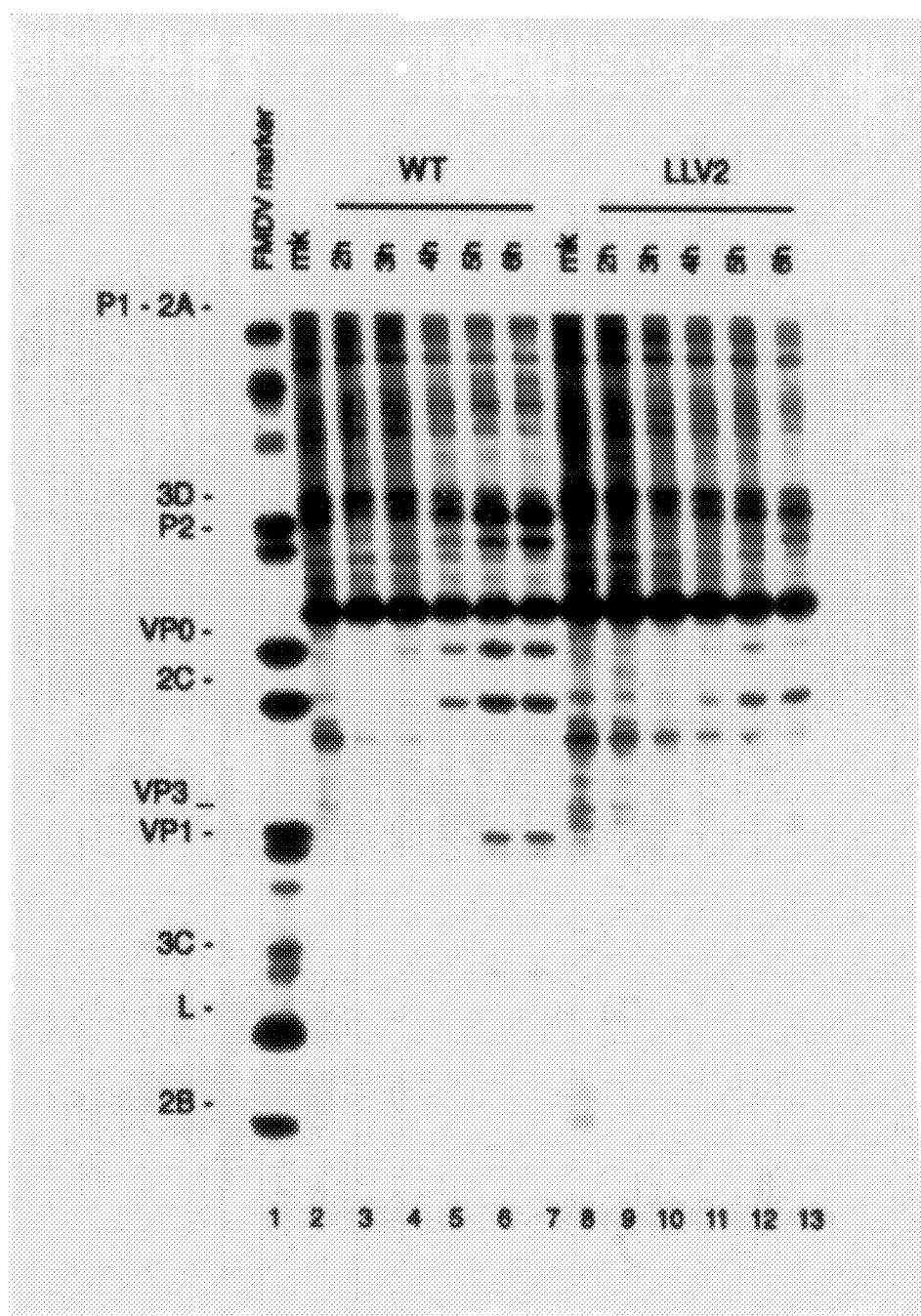
Figure 6:
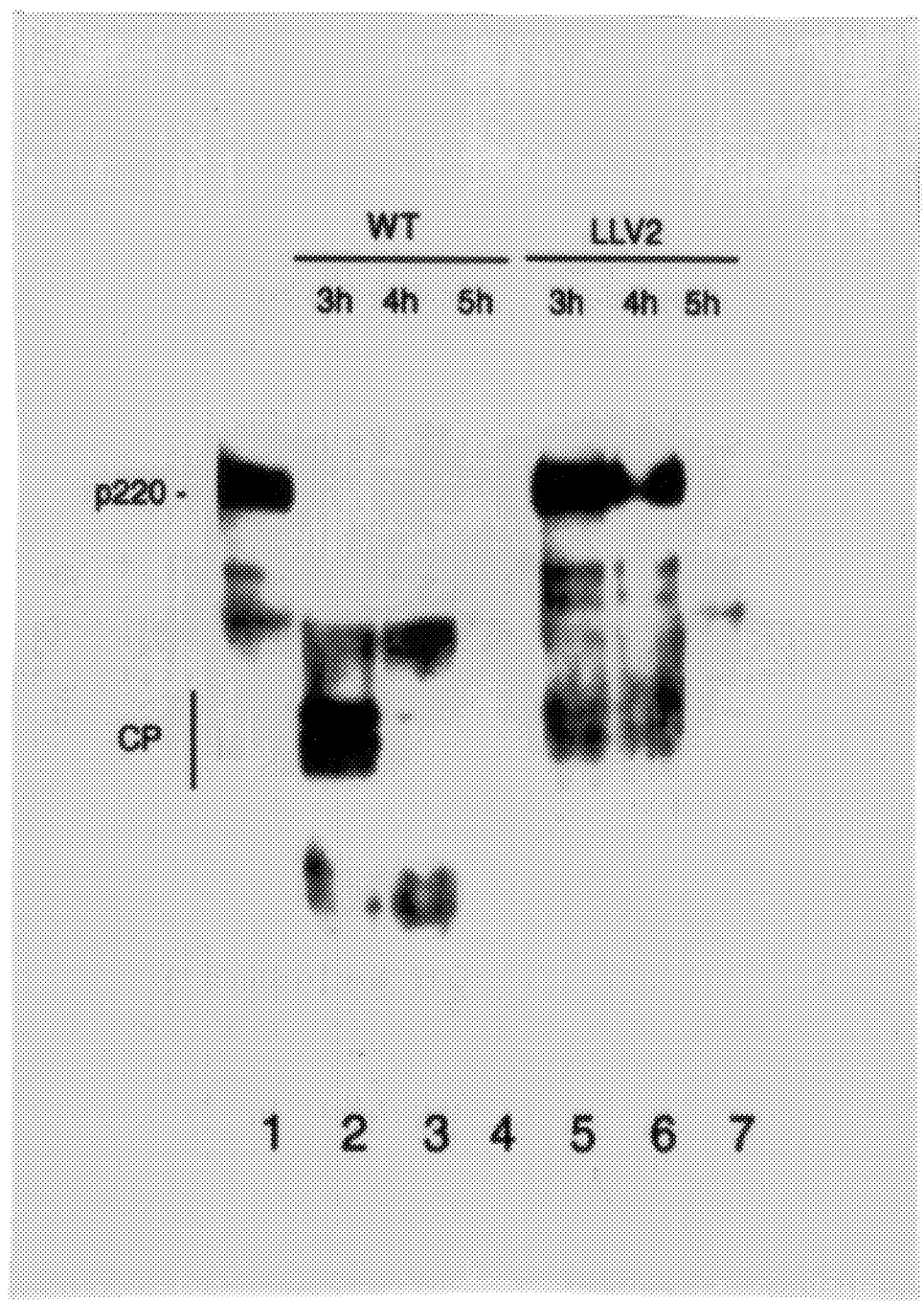

FIG. 4 shows one-step growth curve of molecularly-cloned parent A12-IC (infectious clone) virus and A12-LLV2. BHK-21 cell monolayers were infected with A12-IC or A12-LLV2 at a multiplicity of infection (moi) of 10, rinsed with a pH 6 buffer [to remove residual input virus (Rieder et al., supra), and then incubated at 37° C. The amount of virus released into the culture fluid was determined at each time point by plaque assay.

FIG. 5 shows the qualitative analysis of protein synthesis in A12-IC- and A12-LLV2-infected cell. A12-IC- or A12-LLV2-infected BHK cells were rakiolabeled with 35 S-methionine for 1 hr at various times after infection (lanes 3–7 and 9–13, respectively). Cytoplasmic extracts were prepared, protein synthesis was quantitated by TCA precipitation, and equal amounts of TCA-precipitable protein were resolved by SDS-PAGE on a 15% gel. Lane 1 represents the in vitro translation products of FMD virion RNA, and lanes 2 and 8 are radiolabeled mock-infected (mk) cell extracts.

FIG. 6 shows the analysis of p220 in A12-IC- and A12-LLV2-infected cells. Cytoplasmic extracts from uninfected BK-LF cells (lane 1), A12-IC-infected BK-LF cells (lanes 2–4), or A12-LLV2-infected BK-LF cells (lanes 5–7) at 3, 4 and 5 hr postinfection were prepared and separated by SDS-PAGE. Western blot analysis was performed with polyclonal serum specific for p220. The position of p220 and p220 cleavage products (CP) are indicated.

DETAILED DESCRIPTION OF THE INVENTION

A vaccine is defined herein as a biological agent which is capable of stimulating a protective immune response in an animal to which the vaccine is administered.

Foot-and-mouth disease virus is an RNA virus of the Aphthovirus genus of the family Picornaviridae. There are several known serotypes occurring in Europe (A, O and C serotypes) and southern Africa (SAT 1, SAT 2 and SAT 3) and the Asia 1 serotype, all having distinct variations both immunologically and genetically. The virion consists of a single-strand, positive-sense RNA genome packaged in an icosahedrally symmetric shell composed of 60 copies each of four structural proteins, VP 1–4.

Among the picornaviruses, only members of the Aphthovirus genus contain an active leader (L) proteinase gene. The L proteinase has only two known functions. First, it autocatalytically removes itself from the N-terminus of the elongating viral polyprotein (Strebel and Beck. 1986. *J. Virol.* vol. 58, pp. 893–899). This activity permits N-terminal myristoylation (Chow et al. 1987. *Nature.* vol 327, pp. 482–486) of the exposed N-terminus of the capsid precursor protein P1, which is required for the proper assembly of the viral capsid.

Second, it cleaves the p220 subunit of the eukaryotic initiation factor 4F (eIF-4F), the complex required for the translation of host cellular RNAs. This second activity ensures that viral nucleic acid (which is translated in a p220-independent fashion) is able to outcompete host cell mRNAs for the cellular protein synthesis apparatus. Cleavage of p220 is thought to be responsible for enhancing the translation of viral genes in infected cells, by inhibiting translation of capped host cell mRNAs in the presence of viral translation which occurs by a cap-independent mechanism. Cleavage of p220 appears to be important for picornavirus replication in particular, since the rhinoviruses and enteroviruses utilize a different proteinase (2A) to cleave p220 (Dougherty and Semler. 1993. *Microbiol. Rev.* vol. 57, pp. 781–822). Furthermore, analysis of genetically-engineered poliovirus genomes with mutations in the 2A gene have suggested additional roles for this gene in poliovirus-infected cells (Molla et al. 1993. *J. Virol.* vol 196, pp. 739–747; Yu et al. 1995. *J. Virol.* vol. 69, pp. 247–252). However, virus-specified p220 cleavage is not essential for picornavirus replication of host protein shutoff since cardioviruses do not appear to have a proteinase that cleaves p220 (Mosenkis et al. 1985. *J. Virol.* vol. 54, pp. 643–645).

The FMDV genome contains a single open reading frame (ORF) of about 7,000 bases in length that is translated from an internal ribosome entry site (IRES) which functions to initiate protein translation about 1,100 bases from the 5' end of the RNA (Belsham et al. 1990. *J. Virol.* vol. 64, pp. 5389–5395; Kühn et al. 1990. *J. Virol.* vol. 64. pp. 4625–4631). The viral polyprotein is processed by three viral proteinases co- and post-translationally (see FIG. 1): the leader (L) and 2A proteinases appear to cleave at only a single site in the polyprotein, whereas the 3C proteinase cleaves at multiple sites. The L gene is positioned at the 5' end of the ORF and contains two potential in-frame initiation codons (84 nucleotides apart) which encode proteins defined as Lab and Lb (Rueckert and Wimmer. 1984. *J. Virol.* vol. 50, pp. 957–959), of predicted molecular masses of 23,025 and 19,861 (for type $A_{12}$ viruses) (Piccone et al. 1995. *Virus Res.* vol. 34, pp. 263–275), respectively. Nucleotide sequence analyses have revealed that these two initiation codons are present in representatives of all seven serotypes of FMDV (Clarke et al. 1985. *J. Gen. Virol.* vol. 66, pp. 2615–2626; Sangar et al. 1987. *Nucleic Acids Res.* vol. 15, pp. 3305–3315), and, although the first AUG (at the start of Lab) is not always in a context that should initiate efficiently (Kozak, M. 1986. *Cell.* vol. 44, pp. 282–292), both Lab and Lb have been detected in in vitro translation reactions and in infected cells (Clarke et al., supra; Sangar et al., supra). In addition, the L gene shows sequence similarity to the papain family of proteinases (Gorbalenya et al. 1991. *FEBS Lett.* vol. 288, pp. 201–205), and inhibitor studies (Kleina and Grubman. 1992. *J. Virol.* vol. 66, pp. 7168–7175) and site-directed mutagenesis studies (Piccone et al. 1995. *J. Virol.* vol. 69, pp. 4950–4956) have confirmed that it belongs to this class of proteinases.

To investigate the role of the L proteinase in viral replication, synthetic viral genomes lacking the L gene were generated and their viability tested in cells (Piccone et al. 1995. *J. Virol.* vol. 69, pp. 5376–5382, herein incorporated by reference). To produce leaderless viruses, genomes that initiated translation of the VP4 protein from both of the possible leader initiation codons were designed. It was found that only the genome that initiated polyprotein synthesis at the second L AUG (i.e. Lb AUG) produced a live virus (cDNA clone pRM-LLV2). RNAs in which the polyprotein was positioned behind the first AUG of L (i.e. Lab AUG) were unable to generate live viruses (cDNA clones pRM-LLV1 and pRM-LLV1+), apparently due to the greatly reduced ability of these RNAs to efficiently initiate synthesis of the truncated viral polyprotein at the Lab AUG. These latter two synthetic viral genomes contained either a wild-type sequence preceding the first AUG, UUU, or an altered sequence, GGCC, (cDNA clones pRM-LLV1 and pRM-LLV1+, respectively) to improve translation efficiency; however, both of the sequences tested displayed similar low translational efficiencies in vitro, and synthetic RNAs transcribed from either cDNA failed to produce viable viruses.

To investigate the role of the FMDV L proteinase in viral maturation, host-cell protein synthesis shutoff and viral pathogenesis, and to generate leader-deleted viruses that could serve as live-attenuated FMD vaccines, synthetic full-length cDNAs lacking all or a portion of the L gene were constructed and RNA transcripts transfected into eukaryotic cells.

Figure 1A:
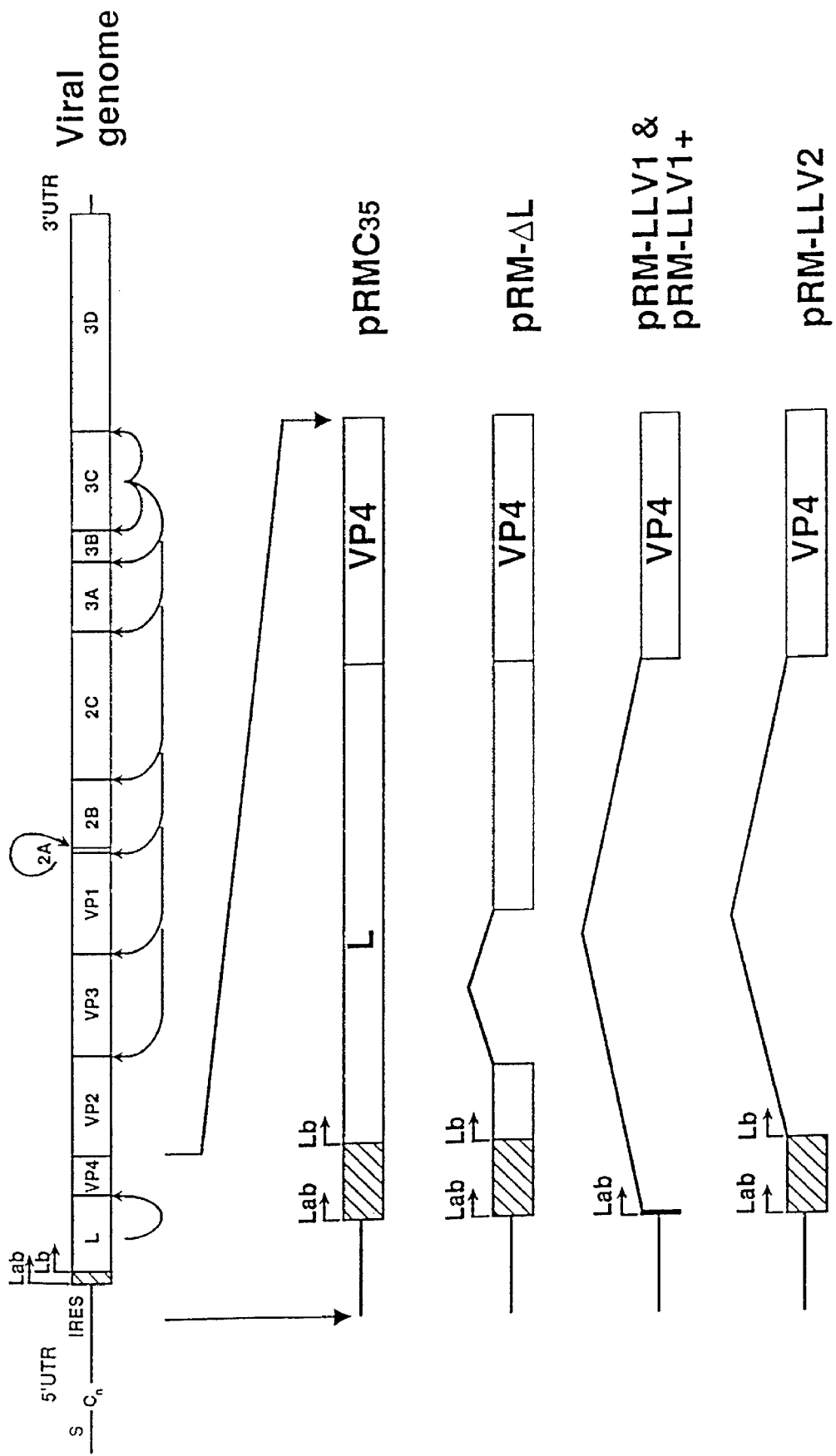
FIG. 1A shows a diagram of the FMDV genome and L-deleted genomes. The viral open reading frame is boxed, and the shaded box corresponds to the 84 nucleotide region between the two in-frame initiation codons for Lab and Lb. Abbreviations used in this figure are: IRES, internal ribosome entry site; $C_n$, poly(C) tract; S, 5' portion of the genome or small fragment; UTR, untranslated region.
Figure 1B:
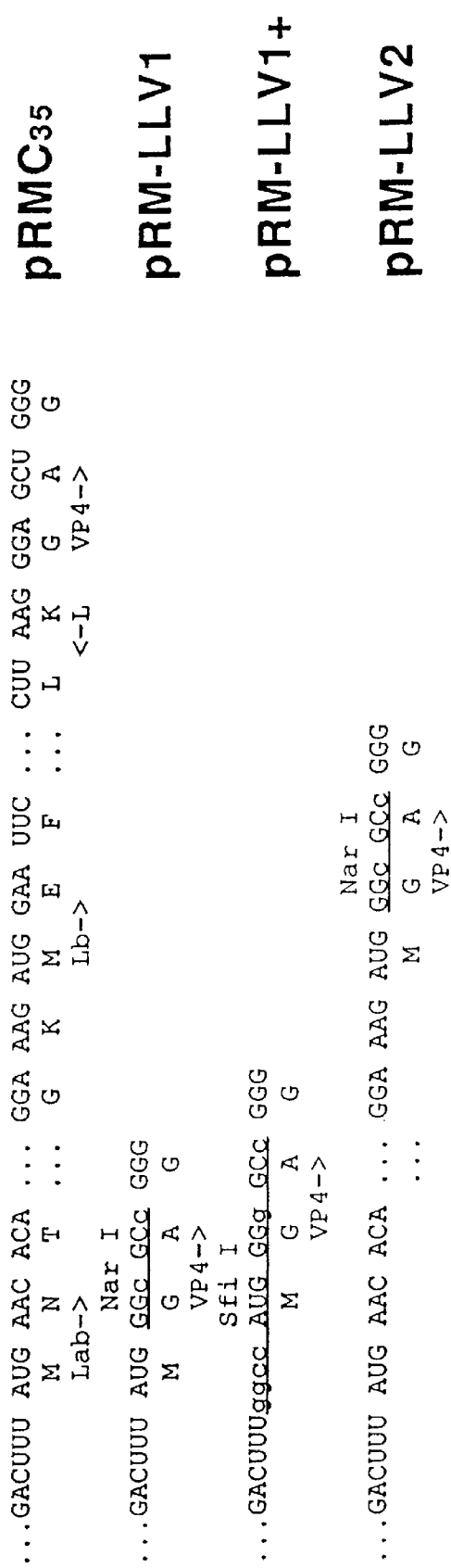
FIG. 1B shows the sequence of the wild type and mutant RNAs surrounding the initiation codons for Lab and Lb and the cleavage site between L and VP0. "..." indicates sequences left out for clarity; underlining indicates the position of restriction endonuclease sites in the cDNA; lower case indicates nucleotides added or changed by site-directed mutagenesis. pRMC$_{35}$ contains the RNA fragments SEQ ID NO: 1, SEQ ID NO: 3 and SEQ ID NO: 5, which respectively code for the corresponding peptides SEQ ID NO: 2, SEQ ID NO: 4 and SEQ ID NO: 6; pRM-LLV1 is SEQ ID NO: 7, which codes for the corresponding peptide SEQ ID NO: 8; pRM-LLV1+ is SEQ ID NO: 9, which codes for the corresponding peptide SEQ ID NO: 10; pRM-LLV2 contains the two RNA fragments SEQ ID NO: 11 and SEQ ID NO: 13, which code for the peptides SEQ ID NO: 12 and SEQ ID NO: 14 respectively.
Figure 2:
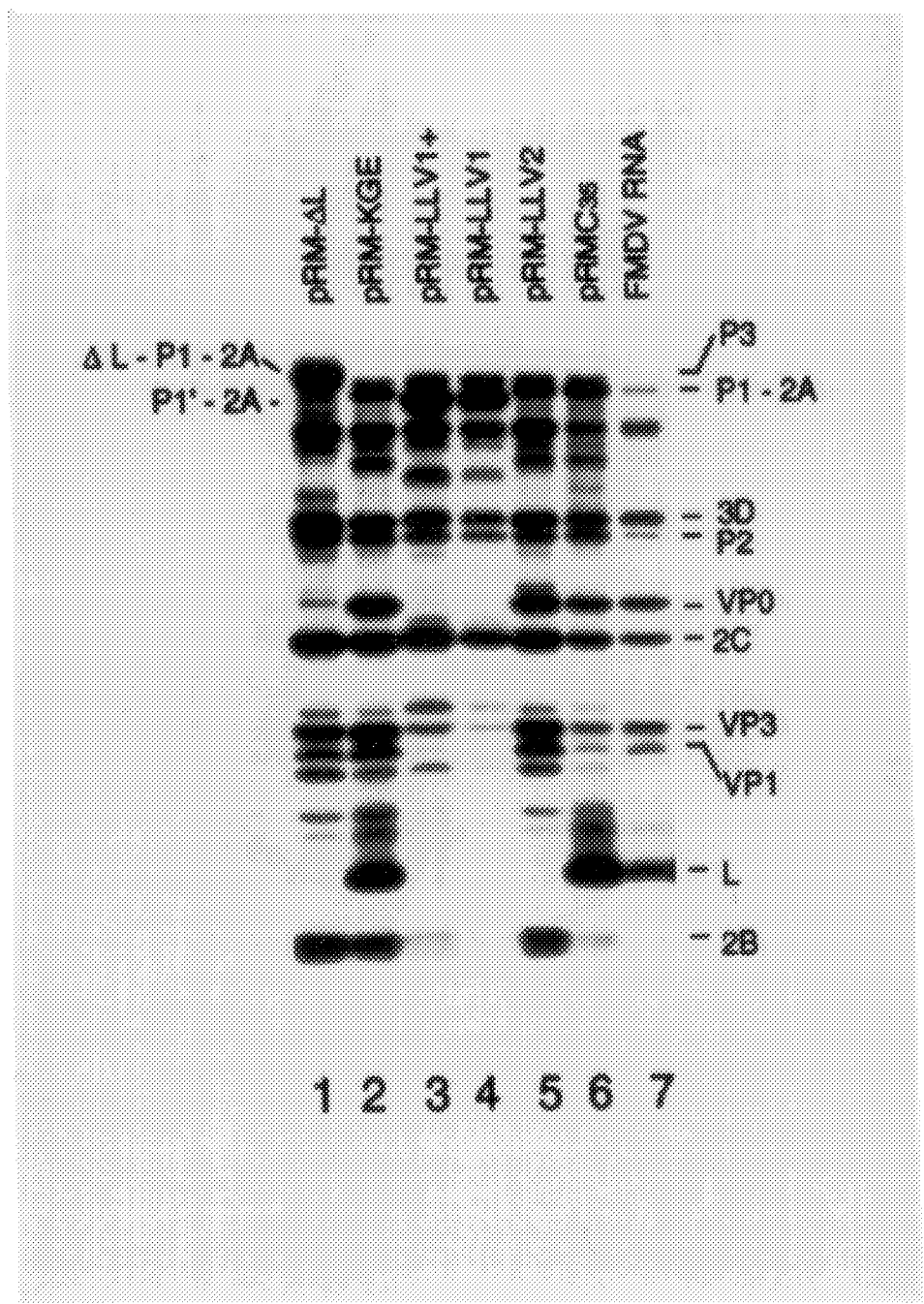
FIG. 2 shows the in vitro translation of FMDV mutant transcripts. Transcripts from cDNAs shown in FIG. 1 were translated in a cell-free system and the radiolabeled products examined by SDS-PAGE on a 15% gel. The designation of each transcript used is indicated at the top of each lane.

Plasmids containing the full-length type A12 cDNA molecules lacking all or a portion of the L gene were constructed by conventional recombinant techniques (FIG. 1A). Plasmids harboring full-length cDNAs containing complete L-deletions were constructed by using polymerase-chain-reaction (PCR) site-directed mutagenesis protocols (Higuchi et al. 1988. *Nucleic Acids Res.* vol. 16, pp. 7351–7367) to introduce novel restriction sites at the junction of the IRES and the VP4 gene. Briefly, plasmids pRM-LLV1 and pRM-LLV2 were constructed by addition of a NarI site encoding Gly-Ala (corresponding to the first two amino acids of VP4) to the initiation codons of Lab or Lb, respectively, and then ligating these segments to a VP4 cDNA containing silent mutations in the first and second codons (Gly-Ala) to produce a second NarI site (see FIG. 1). pRM-LLV1+ contained the Lab initiation codon preceded by an additional 4 bases (GGCC) which were added to produce a better context for translation initiation (Kozak, supra). It was created by addition of an SfiI site at the IRES/VP4 junction (FIGS. 1 and 2).

Following mutagenesis, all plasmid DNAs were sequenced through the entire amplified region using Sequenase (Amersham, Arlington Heights, Ill.). The exact nucleotide sequences surrounding the initiation codons positioned in front of the VP4 coding regions of the three cDNA clones containing complete deletions of L are shown along with WT sequences in FIG. 1B. pRM-ΔL has an in-frame deletion of 192 nucleotides from the center of the L gene which abrogates L function (Piccone et al., *Virus Res.*, supra). pRM-LLV1 contains the Lab AUG positioned in front of the codon corresponding to the N-terminal Gly of VP4. pRM-LLV1+ was constructed using the Lab AUG found in pRM-LLV1, but with modifications of the sequence 5' of the AUG to produce a more favorable context for translation initiation (Kozak, supra), and pRM-LLV2 contains the Lb AUG positioned in front of the same Gly codon of VP4. The genome-length cDNAs present in all of these plasmids were derived from the infectious cDNA clone, pRMC$_{35}$, and were preceded by a synthetic T7 RNA polymerase promoter and followed by a unique NotI site (Rieder et al., supra). Plasmid pRM-KGE contains a mutation in the cell-binding site (Mason et al. 1994. *Proc. Natl. Acad. Sci. USA*. vol. 91, pp. 1932–1936). RNAs transcribed from this cDNA are translated and processed as efficiently as wild type (pRMC$_{35}$) RNA, but cells transfected with pRM-KGE RNA produce virus particles incapable of binding to or infecting cells, thus eliminating their ability to initiate a second cycle of infection in transfection experiments.

T7 transcripts of NotI-linearized plasmid DNA were produced using the MegaScript kit (Ambion, Inc., Austin, Tex.). Transcripts were translated in vitro using reticulocyte lysates as described by Vakharia et al. (1987. *J. Virol.* vol. 61, pp. 3199–3207), or transfected into BHK cells using Lipofectin (GIBCO-BRL, Gaithersburg, Md.) (Rieder et al., supra) or electroporation (Mason et al., supra).

T7 RNA transcripts derived from pRM-KGE, PRM-ΔL, pRM-LLV1, pRM-LLV1+ and pRM-LLV2 were checked for their ability to function as templates for protein synthesis in reticulocyte lysates. It was found that transcripts from pRM-KGE, pRM-ΔL, and pRM-LLV2 were translated in vitro at least ten times more efficiently than transcripts from pRM-LLV1 and pRM-LLV1+ (results not shown). Qualitatively, the translation products produced from transcripts of pRM-KGE and pRM-LLV2 were identical to the products produced by virion RNA, except that the reactions programmed with pRM-LLV2 RNA did not contain L (FIG. 2). The translation products obtained from pRM-LLV1 and pRM-LLV1+ transcripts differed dramatically from those produced by the other transcripts. Neither P1-2A, which includes the structural protein precursor gene (P1) and the 2A gene, nor VP0 was observed, and there were reduced amounts of VP3 and VP1. Instead, a product that migrated more rapidly than P1-2A was observed (P1-2A'), suggesting that its synthesis had initiated at a site within the VP4 coding region (FIG. 2). The nature of this aberrant product was investigated by incubating the pRM-LLV1 or pRM-LLV1+ translation reactions with *Escherichia coli* (*E. coli*)-expressed FMDV 3C proteinase (Bablanian and Grubman. 1993. *Virology.* vol. 197, pp. 320–327). These studies showed that the band that migrated more quickly than P1-2A could be cleaved to products that co-migrated with VP1, VP3, and a third product that migrated faster than VP0 (results not shown).

T7 RNA transcripts derived from pRMC$_{35}$, pRM-ΔL, pRM-LLV1, pRM-LLV1+ and pRM-LLV2 were transfected into monolayers of baby hamster kidney (BHK) cells using Lipofectin (GIBCO-BRL, Gaithersburg, Md.), and the monolayers were stained 72 hours later to reveal plaques. Under these conditions, pRM-LLV2- and pRMC$_{35}$-derived transcripts showed essentially identical specific activities, whereas no plaques were detected in cells transfected with pRM-ΔL, pRM-LLV1 or pRM-LLV1+ RNAs (Table 1). Furthermore, the pRM-LLV2 RNA produced plaques slightly smaller than those produced by the L gene-containing RNA from pRMC$_{35}$ (Table 1).

Five to ten μg of T7 RNA transcript derived from pRM-KGE, pRM-ΔL, pRM-LLV1, pRM-LLV1+ or pRM-LLV2 was transfected into 1.6×10$^7$ BHK cells using electroporation and incubated overnight in the presence or absence of radiolabel (described by Mason et al., supra). Cells transfected with transcripts from pRM-KGE, pRM-ΔL and pRM-LLV2 showed cytopathic effect (CPE) in over 95% of the cells within 16 hours of transfection, whereas cells transfected with pRM-LLV1 and pPM-LLV1+ derived transcripts showed CPE that was indistinguishable from cells electroporated in the absence of

TABLE 1

Characteristics of synthetic RNAs in BHK monolayers transfected using Lipofectin.

| Source of RNA | Specific infectivity[a] | Plaque size |
| --- | --- | --- |
| pRMC$_{35}$ | 3.6 × 10$^{4b}$ | 4–6 mm |
| pRM-LLV1 | nd[c] | |
| pRM-LLV1+ | nd | |
| pRM-LLV2 | 3.3 × 10$^{4b}$ | 2–4 mm |
| pRM-ΔL | nd | |
| pRM-KGE | nd | |

[a]Pfu/μg of synthetic RNA obtained with the indicated plasmids.
[b]Average of 2 preps.
[c]None detected in 250 ng.

TABLE 2

Virulence of the WT virus and LLV2 in suckling mice.

| | Experiment #1 (10-day-old mice) | | | Experiment #2 (7-day-old mice) | | |
|---|---|---|---|---|---|---|
| Virus | pfu/LD$_{50}$ | 100% lethal dose (pfu) | 0% lethal dose (pfu) | pfu/LD$_{50}$ | 100% lethal dose (pfu) | 0% lethal dose (pfu) |
| WT virus | 2 | 44 | 0.04 | 0.9 | 20 | 0.02 |
| LLV2 | 76 | >6 × 10$^4$ | <0.06 | 0.5 | 1.1 × 10$^4$ | <0.01 |

RNA. Since the viral particles produced by pRM-KGE RNA are not infectious (Mason et al., supra), and hence unable to spread between cells following transfection, the extensive CPE observed in these cultures indicated that highly efficient transfection was achieved under these conditions.

Plaque assays performed with freeze-thawed lysates of transfected cultures revealed high titers of virus in cells transfected with RNA from pRM-LLV2, but no virus was detected in cells transfected with RNAs from pRM-KGE, pRM-ΔL, pRM-LLV1, or pRM-LLV1+. Fresh BHK cells were incubated with the freeze-thawed lysates of cells transfected with each of the latter four RNAs, and incubated for an additional 48 hrs at 37° C. The cells remained indistinguishable from uninfected cells, and plaque assays performed on freeze-thawed lysates from these blind passages did not reveal any virus capable of forming plaques on BHK cells.

Radioimmunoprecipitates were prepared from $^{35}$S-methionine-(New England Nuclear, Boston, Mass. or Amersham, Arlington Heights, Ill.) labeled in vitro translation reactions, transfected cells, or infected cells using standard techniques. Immunoprecipitations were performed with MAb (2PD11), which recognizes conformational determinants on the viral capsid (Baxt et al. 1984. *J. Virol.* vol. 51, pp. 298–305; Baxt et al., 1989. *J. Virol.* vol. 63, pp. 2143–2151), or a bovine serum to FMDV. Radio-labelled immunoprecipitates were resolved by electrophoresis on 15% polyacrylamide gels containing sodium dodecyl sulfate (SDS-PAGE) and fluorographed.

Figure 3:
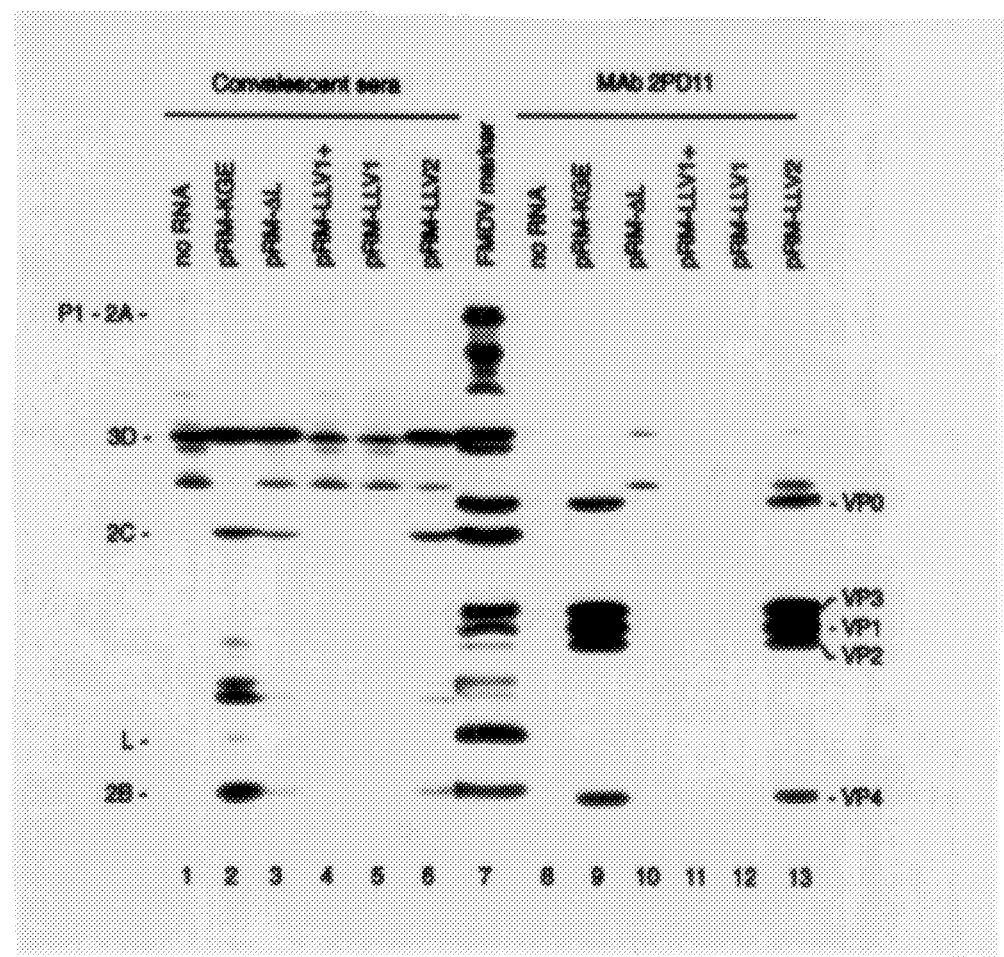
FIG. 3 shows FMDV proteins immunoprecipitated from lysates of cells transfected with RNA transcripts. BHK-21 cells were electroporated with mutant RNAs (as indicated at the top of each lane) and radiolabeled with $^{35}$S-methionine.

SDS-PAGE of immunoprecipitates prepared from radiolabeled, transfected cells confirmed that viral proteins were present in cells transfected with RNAs from pRM-KGE, pRM-ΔL, and pRM-LLV2 (FIG. 3). However, no viral products were detected in cells transfected with RNAs from pRM-LLV1 or pRM-LLV1+ (FIG. 3). Furthermore, analysis of the culture fluid revealed that virions were only efficiently released by cells transfected with pRM-KGE or pRM-LLV2 RNAs (data not shown). These data strongly suggest that the major initiation site used for production of P1-2A from the pRM-LLV2 RNA was the Lb AUG, since only the product of translation from this site could be myristoylated, and myristoylation is important in many steps of picornavirus assembly (Belsham et al. 1991. *J. Gen. Virol.* vol. 72, pp. 747–751; Muscofo et al. 1991. *J. Virol.* vol. 65, pp. 2372–2380).

Virus recovered from cells electroporated with pRM-LLV2 RNA (BHK pass 1) was passaged two additional times in BHK cells, and compared to a BHK pass 3 virus obtained from cells transfected with the WT infectious clone $pRMC_{35}$. As expected, PCR analysis of the genome of the BHK pass 3 virus recovered from pRM-LLV2 transfected cells revealed that it lacked the L gene. Side-by-side comparison of plaque sizes of these viruses on BHK cells showed that the pRM-LLV2-derived virus (A12-LLV2) formed plaques slightly smaller than its wild-type molecularly-cloned parent A12-IC, infectious clone, from serotype A12 119 virus (2 mm versus 4 mm at 40 hrs post inoculation), consistent with data from Lipofectin transfection assays (Table 1). Furthermore, although A12-LLV2 clearly caused CPE on BHK and bovine kidney (BK-LF) cells, the appearance of CPE was delayed relative to A12-IC infections (results not shown), and one-step growth curves of A12-IC and A12-LLV2 virus-infected cells revealed that A12-LLV2 was released from cells slightly more slowly than A12-IC (FIG. 4).

The ability of A12-LLV2 to shut off host cell protein synthesis was evaluated by radiolabeling BHK cells at various times postinfection, and evaluating total protein synthesis by TCA precipitation and specific protein synthesis by polyacrylamide gel electrophoresis. Evaluation of total protein synthesis showed that, like A12-IC, A12-LLV2 reduced the total amount of protein synthesized by infected cells (results not shown). However, the reduction in protein synthesis was delayed relative to A12-IC infection. Furthermore, analysis of the specific protein products produced by infected cells showed that for the A12-IC, there was a rapid increase in viral protein synthesis relative to cellular protein synthesis, which was not as pronounced in A12-LLV2-infected cells (FIG. 5).

Direct demonstration of differences in the stability of p220 in BK-LF cells infected with the A12-IC and A12-LLV2 was evaluated by Western blot assay with a p220-specific antibody (FIG. 6; Kleina and Grubman, supra). These experiments showed that, in contrast to A12-LLV2-infected cells, intact p220 rapidly disappeared from cells infected with A12-IC, and characteristic cleavage products were observed. However, at later times postinfection, intact p220 also disappeared from cells infected with A12-LLV2, suggesting that factors other than the presence of L in infected cells altered the steady state levels of p220. The time of loss of p220 in A12-LLV2-infected cells correlated well with the appearance of CPE and the shutoff of host protein synthesis. It is unclear, however, if the apparent degradation of this translation initiation factor resulted in these changes or if it was a result of the global changes in cellular metabolism that result from virus infection. Interestingly, the degradation of p220 in A12-LLV2-infected cells could be inhibited by treatment of the culture with the cysteine proteinase inhibitor, E-64d (results not shown).

To test further the effect of L on virus biology, the virulence of A12-IC and A12-LLV2 in mice was compared. Dilutions of A12-IC and A12-LLV2 were inoculated into litters of suckling mice, and the 50% lethal doses ($LD_{50}$s) were established using standard techniques (Reed and Muench. 1938. *American J. Hyg.* vol. 27, pp. 493–497). In the first experiment (10-day-old mice), A12-LLV2 was approximately 40-fold less virulent by this criterion (Table 2), however, A12-LLV2 behaved very differently from A12-IC in these experiments. Specifically, the 100% lethal dose for A12-LLV2 corresponded to over 60,000 $LD_{50}$, whereas the uniformly lethal dose of A12-IC was approximately 44 $LD_{50}$ (Table 2). To investigate this phenomenon, a second experiment was performed with slightly younger mice (7-day-old). This experiment revealed nearly identical $LD_{50}$s from the two viruses, but once again the 100% lethal dose for A12-LLV2 was very high, corresponding to approximately 10,000 $LD_{50}$, whereas for A12-IC it was approximately 20 $LD_{50}$ (Table 2). These results are consistent with the possibility that there was a delay in spread of the A12-LLV2 virus, allowing recovery in some animals, and consistent with the observation that CPE and virus replication observed in A12-LLV2-infected cells in culture were delayed relative to A12-IC. Although A12-LLV2 displayed different properties in mice, it was not dramatically attenuated relative to A12-IC. However, since the disease caused by FMDV in baby mice does not resemble FMD, it is possible that A12-LLV2 differs in virulence and pathogenicity relative to A12-IC in livestock.

The finding that viable viruses could be generated only when the polyprotein was initiated from the second AUG (Lb) is consistent with the finding that this site is the primary one used in infected cells. Further support for the finding that a leaderless virus could only be constructed utilizing the LbAUG comes from recent work (Cao et al. 1995. *J. Virol.* vol. 69, pp. 560–563) showing that genetically-engineered viruses with mutations in the Lb AUG were not viable, whereas viruses with mutations in the Lab AUG were.

Characterization of the A12-LLV2 demonstrated that the L proteinase is not required for shutoff of host protein synthesis. Specifically, the leaderless virus formed clear plaques nearly as large as A12-IC and grew nearly as well as A12-IC in liquid culture. A12-LLV2 also caused CPE in infected cells and shut off host protein synthesis, albeit more slowly and less completely than A12-IC. Interestingly, late in infection p220 was degraded in A12-LLV2-infected cells, probably by a cellular cysteine-proteinase since degradation was prevented by the inhibitor E-64d.

The genetically-engineered viruses of the invention can be used as vaccines that are safer than the current inactivated vaccines. Viruses engineered to have a complete deletion of L are able to assemble and grow in cells in culture, but, since they lack L, they are less toxic to infected cells within the animal, producing an attenuated infection. Animals inoculated with A12-LLV2 develop strong immune responses, ensuring their protection from infection by natural virus. The L-deleted virus is stably attenuated since the L gene is one of the genes responsible for virus-induced cell destruction and is completly deleted from the genome. Thus the function of L cannot be reconstituted by mutation of L-deleted viruses.

Characterization of A12-LLV2 in cell culture has shown that it is attenuated in virus growth, in cytopathic effects, shut-off of host cell protein synthesis, and delayed in the induction of viral protein synthesis as compared to A12-IC. Viruses engineered to have a complete deletion of L are able to assemble and grow in cells in culture, but since they lack the L coding region, they grow more slowly than parental virus and do not shut off host protein synthesis.

Animal studies were initiated to determine the degree of attenuation of the L-deleted virus in its natural host. One bovine, 95-4, was infected by intradermal tongue inoculation at 5–8 sites per virus dose with 5, 50, 500 and 5000 plaque-forming units (pfu) of A12-IC pass 4. At 1 day lesions were present at some of the sites inoculated with the two highest doses of virus. By 2 days lesions were present at all of the sites inoculated with the 3 highest virus doses, while 3 out of 8 sites inoculated with the lowest dose of virus showed lesions. By 3 days the sites inoculated with the 3 highest doses showed lesions that coalesced. This animal developed secondary lesions on the tip of the tongue by 3 days.

A second bovine, 95-2, was infected by intradermal tongue inoculation at 5 sites with 725, 7250, 72500 and 725000 pfu of A12-LLV2 pass 4. At 2 days there were very small lesions at all 5 sites of only the highest virus inoculum. By 3 days the lesions described above appeared to be drying up and by day 4 the needle tracts were healing. This animal developed a slight temperature on day 2, but showed no other clinical signs of disease.

A third bovine, 95-3, was inoculated with 5, 50, 500 and 5000 pfu animal-derived FMDV A12 119 as a control. At 3 days, coalescing lesions on the tongue and lesions on the feet indicated systemic spread of the virus.

TABLE 3

Plaque reduction neutralization

| | | Neutralization titer (log $PRN_{70}$) | | |
|---|---|---|---|---|
| Animal # | Inoculum | 14d | 21d | 28d |
| 95-2 | A12-LLV2 | 3.2, 3.2 | 2.9, 2.9 | 3.2 |
| 95-3 | A12 | ND | ND | ND |
| 95-4 | A12-IC | 2.3 | 2.3, 2.9, 3.2 | 3.2, 3.5 |

To examine the immune response of the animals, both bovines were bled at 1, 14, 21 and 28 days post-inoculation. Serum samples were prepared and tested by a plaque reduction neutralization assay in BHK-21 cells using a known amount of A12-IC pass 4. As shown in Table 3, bovine 95-2 developed a high neutralizing antibody titer on day 14 and maintained this titer until day 28. Bovine 95-4 had a slightly lower titer on day 14, that increased on days 21 and 28.

The virulence in bovines of animal-derived FMDV A12-119, A12-IC and A12-LLV2 were compared (Example 2). Data showed that A12-LLV2 was significantly attenuated in bovines compared to its parent, i.e. approximately $10^5$ less virulent (Table 3). It was also shown that A12-LLV2 did not spread systemically and that it did not induce a high neutralizing antibody response.

Tests were also carried out in primary lamb kidney cells and in embryonic bovine kidney cells, which are highly susceptible to the infectious molecularly cloned parental virus A12-IC, and showed that A12-LLV2 was significantly attenuated and not able to spread when cells were infected at a low multiplicity. This suggested that, in the absence of L, some cell types are able to mount an antiviral response.

Animal experiments were then carried out with A12-LLV2 and A12-IC to answer a number of basic questions concerning the potential use of the mutated virus as a vaccine.

The site of initial replication of FMDV was determined (Example 3), and the pathogenesis of A12-IC and A12-LLV2 were compared. It was found that the site of initial infection of FMDV appears to be the lung, specifically the area of the respiratory bronchioles. The parental virus subsequently disseminated to epithelial sites. In contrast, A12-LLV2 did not spread beyond its initial site of replication as if extensive cell-to-cell spread was not able to occur. It may be that lack of the leader proteinase delays the replication of the virus to the point that host defenses are adequately able to deal with the agent so that there is no spread to secondary sites.

The route of inoculation of A12-LLV2 that induced the highest levels of neutralizing antibody activity was determined (Example 4). Results showed that animals inoculated subcutaneously did not develop clinical signs of disease, while those inoculated intramuscularly and intranasally developed only mild fever. Animals inoculated both subcutaneously and intramuscularly developed a serum neutralizing antibody response, while the animal inoculated intranasally did not. The subcutaneous route induced the highest neutralizing antibody response. No virus was present in oropharyngeal (OP) fluids after subcutaneous inoculation.

The efficacy of subcutaneous inoculation of bovines with A12-LLV2 was examined (Example 5), and it was observed that A12-LLV2 was completely attenuated in cattle. The virus induced a serum neutralizing antibody response at least as early as 4 days postinoculation. The control animal did not seroconvert, thus A12-LLV2 was not shed by the infected animals. A low level mucosal neutralizing antibody response was induced. After a severe intradermalingual challenge the two animals that had the highest serum neutralizing antibody response were protected from development of lesions. The remaining animal developed clinical signs of FMD, but these were less severe as compared to the control animal.

The effect of subcutaneous inoculation of bovines with A12-IC vs A12-LLV2 were compared (Example 6). The parental virus A12-IC caused clinical disease in the 3 inoculated animals. By 15 days postinoculation the control animal seroconverted and thus this virus was spread by aerosol from the inoculated animals. The serum neutralizing titers after frank infection with A12-IC are higher than the titers after infection with A12-LLV2. The inoculated animals as well as the control animal that seroconverted were all protected from challenge with virulent bovine passaged A12.

The overall conclusions derived from the studies were that A12-LLV2 was significantly attenuated in cattle compared to its parent, i.e. at least $10^5$ less virulent. The virus did not appear to spread beyond its initial site of infection in the respiratory bronchioles after natural infection. After subcutaneous inoculation, the virus induced a serum neutralizing antibody response at least as early as 4 days postinoculation and a low level mucosal neutralizing antibody response. The serum neutralizing antibody response was significant and lasted at least 35 days after infection. Animals infected with A12-LLV2 did not shed virus. Animals infected once with A12-LLV2 were protected from clinical disease after a severe intradermalingual challenge with virulent homologous virus.

Preparation of the recombinant virus is carried out by conventional genetic engineering techniques which are well-established in the art (as described, for example, in *Current Protocols in Molecular Biology*. 1994. Ausubel et al., eds. J. Wiley & Sons, N.Y.). The preparation steps include 1) synthesizing cDNA from infectious RNA, 2) deleting the sequences coding for the L proteinase, 3) cloning the mutant synthetic cDNA into an effective vector, 4) transcribing RNA containing the deleted sequences from the mutant cDNA, 5) transfecting cells capable of allowing assembly of the mutant virus with transcribed mutant RNA, 6) allowing the RNA to replicate in the transfected cells in order to produce recombinant mutant virus particles and 7) harvesting the recombinant virus particles from the cell cultures.

Infectious RNA is obtained by purification from FMDV preparations (as described by Baxt et al. 1984, supra) and used as a template for reverse transcription to produce cDNA. The second DNA strand is then generated by a DNA-dependent DNA polymerase using standard techniques (Ausubel et al., supra). Effective polymerases include Klenow, DNA polI or Taq polymerase (NEB, Beverly, Mass.; Boeringer Mannheim, Indianapolis, Ind.; GIBCO/BRL, Gaithersburg, Md.). The DNA products are either directly molecularly cloned into an effective plasmid or amplified by the polymerase chain reaction prior to molecular cloning (Ausubel et al., supra). Effective plasmids include but are not limited to those derived from *E. coli* such as the pGEM plasmids (Promega, Madison, Wis.). Plasmids containing virus cDNAs are assembled into genome-length cDNA molecules (Ausubel et al., supra). Some regions of the genome, specifically the extreme 5' end, the extreme 3' end and the poly C tract found near the 5' end of the genome may be produced from synthetic DNA molecules, based on known or predicted sequence data (Rieder et al., supra). cDNA molecules corresponding to the full-length FMDV genome are then placed under the control of an effective promoter (for example, positioned behind the DNA sequence of the T7 bacteriophage polymerase promoter) in a bacterial plasmid vector (such as one derived from pGEM3). Plasmid DNA molecules containing the full-length cDNA are purified from cultures of the *E. coli* harboring the plasmids (Ausubel et al., supra), and the purified DNA is used as a template for RNA polymerase to produce synthetic genome-length RNAs containing insertions, deletions or mutations in the viral genome (Rieder et al., supra). An effective RNA polymerase has been found to be T7 RNA polymerase (GIBCO/BRL, Promega or Ambion, Austin, Tex.).

The synthetic RNA is effectively constructed from the cDNA sequences from which nucleotides coding for the L proteinase have been deleted (leaderless RNA). This deletion occurs as shown in FIG. 1 and as described supra. cDNA molecules containing the deletion are then prepared using standard polymerase chain reaction procedures (Rieder et al., supra) and the entire amplified region sequenced, for example with Sequenase (United States Biochemicals).

Mutated fragments are then introduced into a full-length infectious clone by any standard technique which is effective (for example, as described by Ausubel et al., supra). The mutations are then resequenced in order to ensure that the required deletion is maintained.

RNAs are transcribed, for example from a NotI-linearized plasmid such as that shown in FIG. 1. A Megaprep T7 kit (Ambion) or the method described by van der Werf et al. (1986. *PNAS*. vol. 83, pp. 2330–2334) have been found effective for this purpose. The synthetic RNAs are then introduced into cells capable of allowing replication of the mutant viruses. BHK cells have been found effective for this purpose; however, other cell lines such as Chinese hamster ovary (CHO) are also useful. The cells may be effectively transfected using Lipofectin (GIBCO/BRL) or electroporation as described in Mason et al., supra.

Cells transfected with the leaderless RNA are produced and cultured, and mutant virus particles are found in the culture medium. Any effective culture medium may be used, for example Eagle's minimum essential medium with 10% calf serum and 10% tryptose phosphate broth, supplemented with antibiotics. The mutant virus may then be harvested from the cultures for use as a vaccine.

The vaccine is formulated in an effective immunization dosage with a pharmaceutically acceptable carrier or diluent, such as physiological saline or tissue culture medium. An effective immunization dosage is defined as being that amount which will induce immunity in an animal susceptible to FMDV and protect the animal against challenge by a virulent strain of FMDV. Typically, the vaccine will contain at least about $10^4$ pfu of the virus, and preferably between about $10^6$ to about $10^8$ pfu. The vaccine may be administered subcutaneously, intramuscularly or intranasally.

The recombinant virus was prepared using the infectious cDNA clone pRMC$_{35}$ as the starting material. In order to ensure that the virus is accessible to the public, the plasmid containing the mutant cDNA pRM-LLV2 has been deposited in a recognized depository, the European Collection of Animal Cell Cultures, Centre for Applied Microbiology & Research, Porton Down, Salisbury, Wiltshire, SP4 OJG, UK, as Accession No. 95080111. Effective virus particles can be produced from the deposited plasmid using methods described herein or any others which are effective and well-established in the art.

The following examples are intended only to further illustrate the inention and are not intended to limit the scope of the invention as defined by the claims.

EXAMPLES

Example 1

Cell Lines, Viruses and Plasmids

Virus stocks were prepared and titrated by plaque assay in BHK cells (strain 21, clone 13) as described by Rieder et al., supra, and BK-LF cells were used to assay p220 cleavage activity (Kleina and Grubman, supra). Wild-type FMDV type A$_{12}$ used in all studies was derived from the infectious clone pRMC$_{35}$ (Rieder et al., supra). Plasmid pRM-KGE, which contains a mutation in the sequence encoding the cell binding site, has been described by Mason et al., supra. RNAs transcribed from this cDNA are translated and processed at the same efficiency as WT (pRMC$_{35}$) RNA, but cells transfected with pRM-KGE RNA produce virus particles incapable of binding to or infecting cells, thus eliminating their ability to initiate a second cycle of infection in transfection experiments. Plasmid pRM-ΔL, which has an in-frame deletion of 192 nucleotides from the center of the L gene, has been described by (Piccone et al. *Virus Res.*, supra), and all plasmids used to produce the mutant cDNAs described were derivatives of pRMC$_{35}$.

Neutralization titers were determined by carrying out plaque reduction neutralization assays on all serum samples using FMDV-specific antibody. The presence of virus in OP samples was determined by testing first for CPE, followed by plaque assay. If a positive result was obtained, a plaque reduction neutralization assay was carried out to confirm the presence of FMDV in the sample.

Example 2

Comparison of Virulence of LLV2 and WT Viruses

A steer (95-3) was inoculated at different sites in the tongue with 5, 50, 500, and 5000 pfu animal-derived FMDV A12 119 in 100 μl. A second steer (95-4) was inoculated in the tongue with 5, 50, 500, and 5000 pfu A12-IC, Pass 4 in 50 μl. A third steer (95-2) was inoculated in the tongue with 725, 7250, 72500, and 725000 pfu A12-LLV2, Pass 4 in 50 μl.

Bovines 95-2 and 95-4 were bled on days 14, 21 and 28 post inoculation for plaque reduction neutralization assays, and the results are shown in Table 3.

The animals were observed daily for clinical signs. Animal 95-3 showed some whiteness developing at the two highest doses by 24 hrs. At 48 hrs, all dilutions showed blanched areas, and coalescing lesions were present at the two highest doses. There were also large lesions present at the sites of the two lowest doses. By 72 hrs, all lesions on the tongue were coalesced, indicating systemic spread of the virus.

Animal 95-4 showed some lesions at the two highest doses by 24 hrs, but not all were involved. At 48 hrs, 3 of 8 sites showed lesions at the lowest dose, and feet were beginning to show lesions. At 72 hrs, lesions at the three highest doses were coalescing, and 3 of 8 sites of the lowest dose were showing lesions. There were also secondary vesicles on the tip of the tongue. The feet never developed good vesicles, indicating a limited systemic spread.

Animal 95-2 showed slight lesions (needle tracts) at 3 of 5 sites of the highest dose at 24 hrs. At 48 hrs, very small lesions had appeared at all 5 sites of the highest dose. A temperature of 103° F. was detected. At 72 hrs, the lesions from 48 hrs appeared to be drying up. At 96 hrs, the needle tracts were healing, therefore A12-LLV2 was quite attenuated, and no systemic spread occurred.

Example 3

Determination of Initial Replication Site of FMDV and Comparison of Pathogenesis of A12-LLV2 and A12-IC Viruses Four cows were inoculated by aerosol with FMDV: two with $2 \times 10^8$ pfu A12-IC, pass 4 and two with $2 \times 10^8$ pfu A12-LLV2, pass 4. The animals were monitored clinically and sedated for examination of lesions. At 24 or 72 hrs postexposure (hpe) the animals were euthanized. Animal tissues were examined histologically and for sites of viral replication by in situ hybridization.

There were no abnormal findings with respect to clinical manifestations of the disease in either of the animals infected with A12-LLV2. Only the animal inoculated with A12-IC and euthanized at 72 hpe had clinical disease, i.e. fever, salivation, and lesions. At 24 hrs postinoculation (pi), there was moderate edema of mediastinal lymph nodes, and at 72 hrs pi there were multiple vesicular lesions in three of the four interdigital clefts and on the tongue. All the respiratory lymph nodes in this animal were edematous and hemorrhagic. Histologically, vesicular development was apparent only in this animal. There was a generalized inflammatory involvement of respiratory bronchioles in the animal given A12-IC and euthanized at 24 hpe, with more confined foci at 72 hpe. This animal had a temperature of 103.6° F. at 24 hrs. In contrast, in the animals given A12-LLV2, at 24 hpe respiratory bronchiolar foci were much harder to discern and define and at 72 hpe in the animal given A12-LLV2, no pulmonary changes were discernible.

By in situ hybridization there were distinct differences in replication patterns between the two viruses, especially noticeable in the lung, which appears to be the primary site of replication. An the A12-IC-infected animals the pattern was one of multifocal yet segmentally diffuse areas of viral synthesis. In comparison, in the A12-LLV2 infected animals, the sites of viral replication in the lung were much more localized.

Example 4

Determination of Optimum Route of Inoculation

Two cows were inoculated subcutaneously (SC), 36 with $10^5$ and 31 with $10^7$ pfu A12-LLV2, pass 4; two cows were inoculated intramuscularly (IM), 35 with $10^5$ and 34 with $10^7$ pfu A12-LLV2; and one cow, 37, was inoculated intranasally with $10^7$ pfu A12-LLV2. The animals were monitored for clinical signs, bled on days 1, 15, and 22 postinoculation, and OP samples were taken at days 5, 7, 15, 22. The serum was tested in a plaque reduction neutralization assay. Serum and OP test results are shown in Table 4. The animals inoculated subcutaneously did not develop clinical signs of disease, while the other animals developed only mild fever. The animals inoculated both subcutaneously and intramuscularly developed a serum neutralizing antibody response, while the animal inoculated intranasally did not. The subcutaneous route induced the highest neutralizing antibody response. No virus was present in OP fluids after subcutaneous inoculation.

TABLE 4

| | | Serum Data: | | | |
|---|---|---|---|---|---|
| | | Clinical | Neutralization titer (log $PRN_{70}$) | | |
| Animal # | Route | signs | 0d | 15d | 22d |
| 36 | SC, $10^5$ | 103° F. on day 6 | 0 | 2.6 | 2.0 |
| 31 | SC, $10^7$ | no temp | 0 | 3.8 | 3.5 |
| 35 | IM, $10^6$ | 103.4° F. days 4–6, redness on naries | 0 | 1.9 | 1.6 |
| 34 | IM, $10^7$ | 104.6° F. on day 6, fever days 4–6, slight nasal discharge days 6–7 | 0 | 2.0 | 2.3 |
| 37 | IN, $10^7$ | 103.4° F. and nasal discharge on day 5. | 0 | <0.6 | <0.6 |

TABLE 4-continued

| | | OP Data: | | | |
|---|---|---|---|---|---|
| | | OP Samples* | | | |
| Animal # | Route | 5d | 7d | 15d | 22d |
| 36 | SC, $10^5$ | – | – | – | – |
| 31 | SC, $10^7$ | – | – | – | – |
| 35 | IM, $10^5$ | – | – | – | – |
| 34 | IM, $10^7$ | – | – | + | – |
| 37 | IN, $10^7$ | – | + | – | – |

Example 5

Determination of Efficacy of Subcutaneous Inoculation of Bovines with A12-LLV2 (Challenge Studies)

Three cows, 13, 73 and 74, were inoculated subcutaneously with $10^7$ pfu A12-LLV2, pass 4. A fourth cow, 9, was placed in the same room as the 3 inoculated animals. There were no clinical signs of disease in any of the animals. The four cows were challenged at 35 days postinoculation in the tongue with $10^5$ pfu bovine passaged A12. The animals were bled on days –1, 7, 14, 21, 28 and 35 days postinoculation and days 14, 21, 51 and 58 postchallenge. OP samples were taken on days 2, 4, 8, 15 and 31 postinoculation and days 40, 44, 46, 102, 106 and 108 postchallenge. Serum and OP test results are shown in Table 5.

TABLE 5

| | | Serum Data: | | | | | | | | |
|---|---|---|---|---|---|---|---|---|---|---|
| | | | Neutralization titer (log $PRN_{70}$) | | | | | | | |
| Animal # | Inoculum | Clinical signs | 0d | 4d | 7d | 14d | 21d | 28d | 31d* | 35d | 14d pc |
| 9 | control | none | <0.6 | <0.6 | <0.6 | <0.6 | <0.6 | <0.6 | <0.6 | <0.6 | 4.2 |
| 13 | SC, $10^7$ | none | <0.6 | 1.6 | 2.3 | 2.0 | 2.3 | 2.0 | 0.6 | 2.0 | 4.9 |
| 73 | SC, $10^7$ | none | <0.6 | 2.6 | 3.2 | 2.9 | 2.9 | 2.9 | 0.6 | 2.9 | 4.3 |
| 74 | SD, $10^7$ | none | <0.6 | 2.5 | 2.9 | 3.2 | 3.2 | 3.2 | 0.6 | 2.6 | 4.6 |

*$PRN_{70}$ of 31d nasal secretions.

| | | OP Data: | | | | |
|---|---|---|---|---|---|---|
| Animal # | Inoculum | OP Samples Prechallenge* | | | | |
| | | 2d* | 4d[1] | 8d | 15d | 31d |
| 9 | control | $5.1 \times 10^{7a}$ | no virus at $10^3$ | no virus at $10^2$ | no virus at $10^2$ | no virus at $10^2$ |
| 13 | SC, $10^7$ | $8.7 \times 10^{7a}$ | $2 \times 10^{7a}$ | $3.8 \times 10^{6a}$ | " | " |
| 73 | SC, $10^7$ | $1.4 \times 10^{8a}$ | $3.7 \times 10^{7a}$ | no virus at $10^2$ | " | " |
| 74 | SC, $10^7$ | $2.8 \times 10^{7a}$ | $8.25 \times 10^{5b}$ | $5 \times 10^{7a}$ | " | " |

| | | OP Samples Postchallenge[2] | | | | | |
|---|---|---|---|---|---|---|---|
| Animal # | Inoculum | 40dpc | 44dpc | 46dpc | 102dpc | 106dpc | 108dpc |
| 9 | control | $3.5 \times 10^{8c}$ | no samples | $5 \times 10^{4c}$ | no virus at $10^2$ | no virus at $10^2$ | no virus at $10^2$ |
| 13 | SC, $10^7$ | no virus at $10^2$ | no virus at $10^2$ | no virus at $10^2$ | no virus at $10^2$ | no virus at $10^2$ | no virus at $10^2$ |
| 73 | SC, $10^7$ | no virus at $10^2$ | $1.7 \times 10^{4c}$ | no virus at $10^2$ | no virus at $10^2$ | no virus at $10^2$ | no virus at $10^2$ |

TABLE 5-continued

| 74 | SC, $10^7$ | no virus at $10^2$ | no virus at $10^2$ | no virus at $10^2$ | no virus at $10^2$ | no virus at $10^2$ | no virus at $10^2$ |

*Titer (pfu/ml) after 1st passage in BHK-21 cells. Plaque assay developed after 2 days. If virus present a plaque reduction neutralization (PRN) assay was done using a serum (1:20 final conc.) from a bovine vaccinated with BEI-A12 as well as serum (1:20 final conc.) from a normal bovine. 1st passage also examined by PCR using primers from the 3D region.
[1]4dpi OP sample from bovine #73, ie., 1° pass BHK-21 cells, is not neutralized by BVDV antiserum.
[2]Under EM 2d OP samples, ie., 1° pass BHK-21 cells, from bovines 9 and 13 one can see ~70 nm particles. After 1 pass of this supernatant on LK cells, one sees ~24 nm particles in the EM.
[a]mixed population, ie., tiny plaques <1 mm and small plaques ~1 mm. By PRN this is not FMDV.
[b]large plaques ~2–3 mm. By PRN this is not FMDV.
[c]large plaques, 4–5 mm. By PRN this is FMDV. However, there is also a low level contamination with small plaque virus that is not neutralized by FMDV serum.

The animals inoculated with A12-LLV2 did not develop any clinical signs of disease. Upon challenge, control animal 9 developed clinical signs of FMD. Bovines 73 and 74 did not develop lesions, while 13 developed some lesions, but their appearance was delayed as compared to the control animal. Results are shown in Table 6.

Example 6

Comparison of Subcutaenous Inoculation of Bovines with A12-IC and A12-LLV2

Three cows 40, 47 and 58, were inoculated subcutaneously with $10^7$ pfu A12-IC, pass 4. A fourth cow, 56, was placed in the same room as the 3 inoculated animals. The animals were monitored for clinical signs and were bled on days 0, 4, 8, 15, 22, 29 and 36 postinoculation. OP samples were taken on days 8, 15, 22 and 30 postinoculation. Serum and OP test results are shown in Table 6.

The four cows were challenged in the tongue at 36 days postinoculation with $10^5$ pfu passaged A12 and bled on day 14 postchallenge. OP samples were taken on days 50, 54, 56 and 76 postchallenge.

The inoculated animals developed clinical signs of FMD, but the control animal did not. Upon challenge, neither the inoculated animals nor the control animal developed FMD.

TABLE 6

| | | | Neutralization titer (log $PRN_{70}$) | | | | | | | |
|---|---|---|---|---|---|---|---|---|---|---|
| Animal # | Inoculum | Clinical signs | 0d | 4d | 8d | 15d | 22d | 29d | 36d | 37d* | 13pc |
| 56 | none | none | 0.6 | 0.6 | 0.6 | 3.8 | 3.6 | 3.3 | 3.3 | 1.5 | 3.5 |
| 40 | SC, $10^7$ | fever, nasal discharge | <0.6 | 2.6 | 4.1 | 3.9 | 3.9 | 4.3 3.9 | 3.6 | 1.8 | 3.3 |
| 47 | SC, $10^7$ | fever, lesions | <0.6 | 2.6 | 4.1 | 3.9 | 3.6 | 3.3 | 3.6 | >2.1 | 3.3 |
| 58 | SC, $10^7$ | fever, lesions | 0.6 | 1.5 | 3.9 | 4.2 | 4.2 | 4.3 | 3.9 | 1.2 | 3.6 |

*Nasal secretions

OP Data:

| | | OP Samples* | | | | | | | |
|---|---|---|---|---|---|---|---|---|---|
| Animal # | Inoculum | 8dpi | 15dpi | 22dpi | 30dpi | 50dpc | 54dpc | 56dpc | 76dpc |
| 56 | control | $2.1 \times 10^{6a}$ | no virus at $10^2$ | no virus at $10^2$ | $1.8 \times 10^{7a}$ | no virus at $10^2$ | no virus at $10^2$ | no virus at $10^2$ | no virus at $10^2$ |
| 40 | SC, $10^7$ | no virus at $10^2$ | no virus at $10^2$ | no virus at $10^2$ | no virus at $10^2$ | no virus at $10^2$ | no virus at $10^2$ | no virus at $10^2$ | no virus at $10^2$ |
| 47 | SC, $10^7$ | no virus at $10^2$ | $8.3 \times 10^{6a}$ | no virus at $10^2$ | no virus at $10^2$ | no virus at $10^2$ | no virus at $10^2$ | no virus at $10^2$ | no virus at $10^2$ |
| 58 | SC, $10^7$ | no virus at $10^2$ | no virus at $10^2$ | no virus at $10^2$ | no virus at $10^2$ | no virus at $10^2$ | no virus at $10^2$ | no virus at $10^2$ | no virus at $10^2$ |

*Titer after 1st passage in BHK-21 cells. Plaque assay developed after 2 days. If virus present a PRN assay was done using a 1:20 dilution (final conc.) of normal bovine serum and a 1:20 dilution (final conc.) of serum from a bovine vaccinated with BEI-A12. 1st passage also examined by PCR using primers from the 3D region.
[a]Plaque size 4–5 mm. By PRN #56 8d and #47 15d are FMDV, but there are microscopic plaques in #47 that are not neutralized by FMDV specific serum.

All references contained herein are herein incorporated by reference.

We claim:

1. A live recombinant foot-and-mouth disease virus, wherein said virus lacks an active leader (L) proteinase protein, the Lb portion of the protein having been deleted.

2. A recombinant foot-and-mouth disease virus genomic RNA, wherein the RNA lacks the sequence encoding the Lib portion of the leader (L) proteinase and is capable of producing the virus of claim 1.

3. A recombinant foot-and-mouth disease virus cDNA, wherein the cDNA lacks the sequence resulting in the Lib portion of the leader (L) proteinase and is capable of producing the RNA of claim 2.

4. A vaccine comprising a viral agent in an effective immunization dosage wherein said viral agent is the recombinant foot-and-mouth disease virus of claim 1 and a pharmaceutically acceptable carrier or diluent.

5. A method of conferring immunological protection against foot-and-mouth disease comprising inoculating an animal susceptible to infection by foot-and-mouth disease virus with an effective immunization dosage of a vaccine comprising a viral agent and a pharmaceutically acceptable carrier or diluent, wherein said viral agent is the recombinant foot-and-mouth-disease virus of claim 1.

* * * * *

UNITED STATES PATENT AND TRADEMARK OFFICE
CERTIFICATE OF CORRECTION

PATENT NO. : 5,824,316
DATED : 10/20/98
INVENTOR(S) : Marvin J. Grubman, Peter W. Mason, Maria E. Piccone and Elizabeth Rieder It is certified that error appears in the above-identified patent and that said Letters Patent is hereby corrected as shown below:

Claim 2, line 2, replace "Lib" with "Lb"

Claim 3, line 2, replace "Lib" with "Lb"

Signed and Sealed this

Sixteenth Day of March, 1999

Attest:

Q. TODD DICKINSON

Attesting Officer  Acting Commissioner of Patents and Trademarks

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
        ( A ) ORGANISM: Foot and mouth disease virus ( i x ) FEATURE:
( A ) NAME/KEY: CDS
( B ) LOCATION: 7..15

( x i ) SEQUENCE DESCRIPTION: SEQ ID NO:1:

```
GACUUU AUG AAC ACA                                                        15
       Met Asn Thr
         1
```

( 2 ) INFORMATION FOR SEQ ID NO:2:

( i ) SEQUENCE CHARACTERISTICS:
( A ) LENGTH: 3 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Asn Thr
  1
```

( 2 ) INFORMATION FOR SEQ ID NO:3:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
( A ) ORGANISM: Foot and mouth disease virus ( i x ) FEATURE:
( A ) NAME/KEY: CDS
( B ) LOCATION: 1..15

( x i ) SEQUENCE DESCRIPTION: SEQ ID NO:3:

```
GGA AAG AUG GAA UUC                                                       15
Gly Lys Met Glu Phe
  1               5
```

( 2 ) INFORMATION FOR SEQ ID NO:4:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Gly  Lys  Met  Glu  Phe
 1                    5
```

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
        ( A ) ORGANISM: Foot and mouth disease virus ( i x ) FEATURE:
        ( A ) NAME/KEY: CDS
( B ) LOCATION: 1..15

( x i ) SEQUENCE DESCRIPTION: SEQ ID NO:5:

CUU AAG GGA GCU GGG 15
Leu Lys Gly Ala Gly
1 5

( 2 ) INFORMATION FOR SEQ ID NO:6:

( i ) SEQUENCE CHARACTERISTICS:
( A ) LENGTH: 5 amino acids
( B ) TYPE: amino acid
( D ) TOPOLOGY: linear ( i i ) MOLECULE TYPE: protein ( x i ) SEQUENCE DESCRIPTION: SEQ ID NO:6:

Leu Lys Gly Ala Gly
1 5

( 2 ) INFORMATION FOR SEQ ID NO:7:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
( A ) ORGANISM: Foot and mouth disease virus ( i x ) FEATURE:
( A ) NAME/KEY: CDS
( B ) LOCATION: 7..18

( x i ) SEQUENCE DESCRIPTION: SEQ ID NO:7:

GACUUU AUG GGC GCC GGG 18
Met Gly Ala Gly
1

(2) INFORMATION FOR SEQ ID NO:8:

(i) SEQUENCE CHARACTERISTICS:
(A) LENGTH: 4 amino acids
(B) TYPE: amino acid
(D) TOPOLOGY: linear (ii) MOLECULE TYPE: protein (xi) SEQUENCE DESCRIPTION: SEQ ID NO:8:

Met Gly Ala Gly
1

(2) INFORMATION FOR SEQ ID NO:9:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: RNA (genomic)

(iii) HYPOTHETICAL: NO (iv) ANTI-SENSE: NO (vi) ORIGINAL SOURCE:
(A) ORGANISM: Foot and mouth disease virus (ix) FEATURE:
(A) NAME/KEY: CDS
(B) LOCATION: 11..22

(xi) SEQUENCE DESCRIPTION: SEQ ID NO:9:

GACUUUGGCC AUG GGG GCC GGG 22
Met Gly Ala Gly
1

(2) INFORMATION FOR SEQ ID NO:10:

(i) SEQUENCE CHARACTERISTICS:
(A) LENGTH: 4 amino acids
(B) TYPE: amino acid
(D) TOPOLOGY: linear (ii) MOLECULE TYPE: protein (xi) SEQUENCE DESCRIPTION: SEQ ID NO:10:

Met Gly Ala Gly
1

(2) INFORMATION FOR SEQ ID NO:11:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: RNA (genomic)

(iii) HYPOTHETICAL: NO (iv) ANTI-SENSE: NO (vi) ORIGINAL SOURCE:
(A) ORGANISM: Foot and mouth disease virus -continued (ix) FEATURE:
    (A) NAME/KEY: CDS
    (B) LOCATION: 7..15

(xi) SEQUENCE DESCRIPTION: SEQ ID NO:11:

```
GACUUU AUG AAC ACA                                          15
       Met Asn Thr
        1
```

(2) INFORMATION FOR SEQ ID NO:12:

(i) SEQUENCE CHARACTERISTICS:
        (A) LENGTH: 3 amino acids
        (B) TYPE: amino acid
        (D) TOPOLOGY: linear (ii) MOLECULE TYPE: protein (xi) SEQUENCE DESCRIPTION: SEQ ID NO:12:

```
Met Asn Thr
 1
```

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: NO (vi) ORIGINAL SOURCE:
        (A) ORGANISM: Foot and mouth disease virus (ix) FEATURE:
        (A) NAME/KEY: CDS
        (B) LOCATION: 1..18

(xi) SEQUENCE DESCRIPTION: SEQ ID NO:13:

```
GGA AAG AUG GGC GCC GGG                                     18
Gly Lys Met Gly Ala Gly
 1               5
```

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:14:

```
Gly Lys Met Gly Ala Gly
 1               5
```